United States Patent [19]

von Smolinski et al.

[11] 3,973,911

[45] Aug. 10, 1976

[54] SULFUR OXIDE DETERMINATION

[75] Inventors: Alfred von Smolinski; Kuo-Chuan Feng, both of Bensenville, Ill.

[73] Assignee: University of Illinois Foundation, Urbana, Ill.

[22] Filed: Feb. 6, 1975

[21] Appl. No.: 547,592

[52] U.S. Cl. .................... 23/230 R; 23/232 R; 23/253 R; 23/254 R; 250/461 R; 252/408
[51] Int. Cl.² ................. G01N 21/38; G01N 31/00
[58] Field of Search ......... 23/230 R, 232 R, 254 R, 23/232 E, 254 E, 255 R, 255 E, 253 R; 252/408; 250/461, 361 C, 365

[56] References Cited
UNITED STATES PATENTS

| | | | |
|---|---|---|---|
| 3,302,023 | 1/1967 | Schachter | 250/365 |
| 3,528,779 | 9/1970 | Fontijn | 23/232 E |
| 3,566,114 | 2/1971 | Brewer | 250/365 X |
| 3,659,100 | 4/1972 | Anderson et al. | 23/232 R |
| 3,746,513 | 7/1973 | Warnick et al. | 23/232 R |
| 3,829,696 | 8/1974 | Birnbaum | 250/365 |
| 3,856,473 | 12/1974 | Dillon | 23/254 E |

*Primary Examiner*—Joseph Scovronek
*Attorney, Agent, or Firm*—Merriam, Marshall, Shapiro & Klose

[57] ABSTRACT

Disclosed are systems, methods and materials for use in detection and quantification of sulfur oxides in a fluid sample. Involved is the reaction of a selected compound which is substantially non-fluorescent under given reaction conditions, e.g., 5-amino-3-sulfosalicylic acid in a pH 1–3 solution, with sulfur oxides in the fluid sample to form a fluorescent reaction product which may be quantified by standard fluorometric techniques.

12 Claims, 4 Drawing Figures

SULFUR OXIDE DETERMINATION

BACKGROUND

The present invention relates generally to sulfur oxide detection and more particularly to systems, methods, and materials for fluorometric detection and quantification of sulfur dioxide in a fluid sample. As used herein, the term "sulfur oxide" includes gaseous sulfur dioxide and its aqueous solutions, as well as sulfurous acid and its salts, but does not include sulfur trioxide, sulfuric acid, or its salts.

The instrumental methods utilized in the analysis of sulfur dioxide can be broken down according to four basic detection principles: colorimetry, conductivity, coulometry and flame photometry. (See, e.g., Coloff, S. G., et al., Amer. Lab., 5, pp. 10–22 (July, 1973).) Additionally, U.S. Pat. No. 3,659,100 relates to the use of the luminescent material, 5-amino-2,3-dihydro-1,4-phthalazinedione, commonly known as "luminol".

The most common of presently utilized methods employ colorimetric techniques and numerous analytical schemes involving such techniques have been suggested. U.S. Pat. No. 3,567,392, for example, relates to the use of a p-aminophenylazobenzene dye.

In 1971 the United States Environmental Protection Agency established national ambient air quality standards for major air pollutants including sulfur dioxide (Federal Register Vol. 36, No. 84, pages 8186–8201). The E.P.A. standards include a "reference" analytical method for sulfur dioxide determination [generally according to West, P. W., et al., Anal. Chem., 28, pp. 1816–19, (1956), as modified according to Scarangelli, F. P., et al., Anal. Chem., 39, pp. 1709–1719 (1967)]. The method involves collection and absorption of sulfur dioxide in sodium or potassium tetrachloromercurate (TCM) to form a dichlorosulfitomercurate solution. The absorbed sample is reacted in an analytical system with formaldehyde and a free amino-containing dyestuff, para-rosaniline. Spectrophotometric analysis of the resulting para-rosaniline methylsulfonic acid permits quantification of "trapped" sulfur dioxide. According to this method, concentrations of sulfur dioxide in the range of 26 to 1,050 $\mu g/m^3$ (0.01 to 0.40 parts per million) may ordinarily be measured without sampling very large volumes of air. The lower limit of detection is approximately 0.05 $\mu g/ml$. of sulfur dioxide in the TCM trapping solution.

The use of the para-rosaniline method is by no means free of problems. It has been noted, for example, that multiple reactions occur between the para-rosaniline (which has multiple free amino sites) and the formaldehyde-bisulfite complex which is an intermediate in the Schiff reaction method. Further, it has been noted that many para-rosaniline samples obtained from various manufacturers contain impurities which may lead to analytical errors. Stock solutions of the para-rosaniline reagent ordinarily must be made up three days in advance of use. For adequate reproducibility, a closely monitored temperature of 45°C. and a 30 minute development time is recommended.

In an attempt to avoid the apparently insoluble problems associated with the reference spectrophotometric method, numerous variant techniques have been proposed. Axelrod, H. D., et al., Anal. Chem., 42, pp. 512–515 (1970), for example, suggests the use of a similar Schiff reaction within a more sensitive fluorometric analytical procedure according to which the inherent fluorescence of 5-aminofluorescein is quenched in the course of a reaction with a formaldehyde-bisulfite complex. This method too has a rather long recommended development time. Employing a 5 $\times$ 10$^{-4}$ M fluorescein reagent, the method has a lower detection limit of approximately 0.03 $\mu g/ml$. sulfur dioxide in a TCM trapping solution. With the fluorometer reagent blank reading set at 100, such a "lower limit" reaction mixture gives a reading of about 98 after 15 minutes of development. As such, the method is less than optimally satisfactory in rapid analysis of multiple samples which differ in sulfur dioxide content by small amounts.

To date, no direct fluorometric sulfur oxide measurement scheme has been elucidated wherein a relatively non-fluorescent reagent proportionally reacts with the oxide to form quickly and easily measurable amounts of a fluorescent moiety.

BRIEF DESCRIPTION

According to the present invention, sulfur oxides in a fluid sample may be reacted, under appropriate reaction conditions, with a substantially non-fluorescent material such as 5-amino-3-sulfo-salicylic acid to form a fluorescent moiety which may be subjected to standard fluorometric quantification analysis. Fluid samples examined for sulfur oxide content may be liquid or gaseous and may include both the "original" medium (e.g., air under ambient conditions or a wastewater aliquot) or a medium in which sulfur oxide has been collected or absorbed (e.g., a TCM trapping solution). Contemplated by the invention are instrumental systems for random and/or continuous monitoring of fluid samples as well as reagents especially suited for use in developing the desired fluorescent reaction product for fluorometric analysis.

Further aspects and advantages of the invention will be understood upon consideration of the following detailed description, reference being made to the drawing wherein.

DETAILED DESCRIPTION

The present invention is generally involved with a direct fluorometric method for sulfur oxide determination wherein a liquid or gaseous fluid sample is contacted with an aqueous reagent including a selected substantially non-fluorescent compound. As employed herein, the term "substantially non-fluorescent" includes compounds which display no fluorescence under pertinent reaction conditions as well as compounds which display fluorescence so weakly that such fluorescence may be effectively "zeroed" in the course of running a fluorometric reagent blank. Under appropriate conditions of pH, and in the presence of a suitable Schiff reaction aldehyde component such as formaldehyde, there is formed a relatively strongly fluorescent moiety, the presence of which may be detected and quantified. Preferred compounds for use in the reagents of the invention include those having a single free amino group "active" site as this characteristic will enhance the linear proportionality of the formation of the desired fluorescent moiety. The selected compound should be at least slightly soluble in aqueous media and should be readily obtainable in relatively pure form. Reagents for use according to the invention containing the selected compound should be quickly and easily prepared and should also have good shelf-life characteristics. Further, it should be relatively non-reactive with common fluid sample components (e.g., ozone in air samples) other than sulfur oxides, so that interferences with the desired reaction will be minimized.

Figure 4:
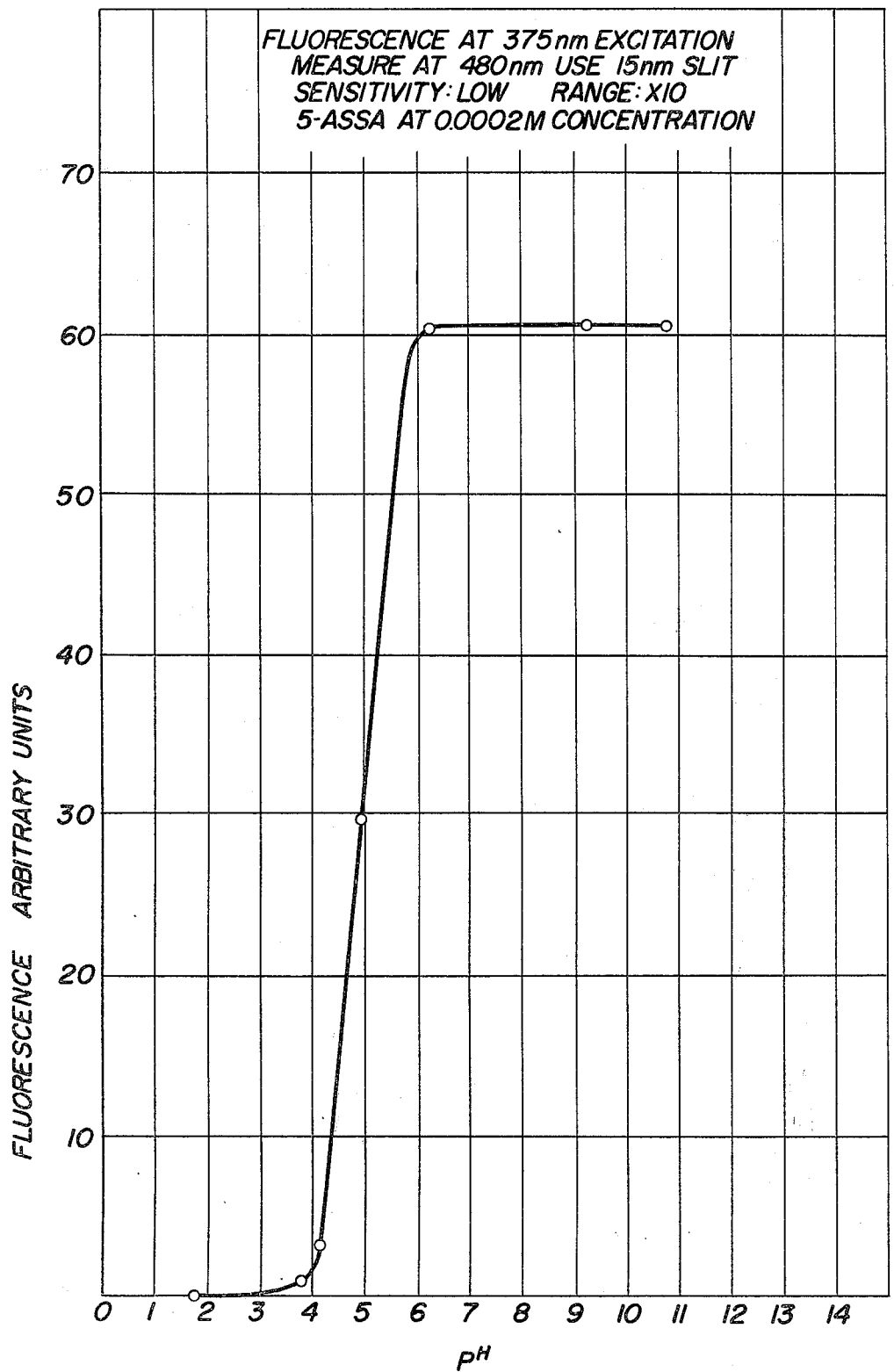

A much preferred compound for use in this respect is 5-amino-3-sulfo-salicylic acid (hereafter 5-ASSA). The compound is also known in the art as 5-amino-2-hydroxy-3-sulfobenzoic acid (M.W. 233.20). A reagent including an aqueous solution of 5-ASSA may be easily prepared. At a reagent pH of less than about 2.0, a 0.0002 M solution of 5-ASSA exhibits little or no fluorescence (excitation at 375 nm, slit 15 nm; emission at 480 nm, slit 60 nm) as generally illustrated in FIG. 4. When the same reagent is contacted with a fluid sample containing sulfur dioxide and a formaldehyde Schiff reaction component, a moiety which is strongly fluorescent (when examined under the same excitation and emission parameters) is formed in substantially direct proportion to the quantity of sulfur dioxide present in the sample. Comparison of the relative fluorescence of the fluid sample reaction product with that of reaction products formed using standardized sample quantities of sulfur dioxide will result in derivation of the desired quantitative data regarding the sulfur dioxide content of the fluid sample.

While the precise reaction involved in the above-described formation of a fluorescent moiety is presently not fully ascertained, it is believed to be the following:

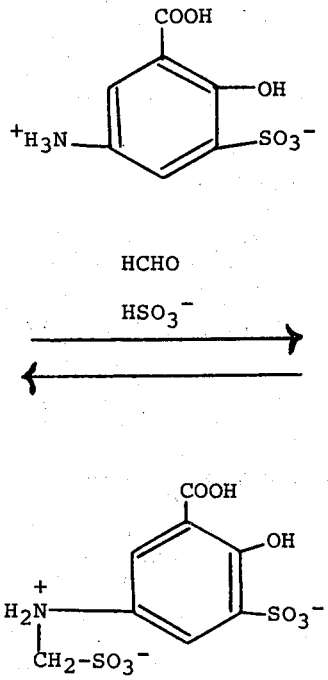

The following examples further illustrate practice of the invention in analysis of fluid samples for sulfur dioxide.

EXAMPLE I

A sulfur dioxide determination procedure was run for purposes of generally comparing the accuracy of methods of the invention to the modified West, et al. procedure, infra.

A. Preparation of Materials and Reagents

1. Stock Sulfur Dioxide/Sodium Tetrachloromercurate Solution

A stock sulfur dioxide/sodium tetrachloromercurate solution was obtained through suitable combination of a 0.04 M sodium tetrachloromercurate solution (prepared by standard techniques from mercuric chloride and sodium chloride) and an iodometrically verified solution of sodium meta-bisulfite of known molarity. The stock had a final sulfur oxide concentration equivalent to 5.1 $\mu$g./ml.

2. Formaldehyde Solution

A 4% formaldehyde solution was prepared through dilution of 40% (v/v) formaldehyde with distilled water.

3. 5-ASSA Solution

A 0.002 M. solution of 5-ASSA in 1.7% phosphoric acid was prepared.

4. Para-rosaniline Solution

A para-rosaniline solution for use in the colorimetric method was prepared according to the modified West, et al. procedure, infra.

B. Instrumentation

Fluorometric determinations were made on a Turner Model 430 Spectrofluorometer using a one centimeter square quartz cell. Excitation, emission and range settings employed are shown on Table 1 below.

Colorimetric determinations were made on a Perkin-Elman Model 200 colorimeter using a one centimeter quartz cell and absorbance was determined at 549 nm.

C. Procedure

Dilutions of the stock sulfur dioxide/sodium tetrachloromercurate solution were made. Preparation of a typical 25 ml. reaction mixture involved admixing 10.0 ml. of tenfold diluted (i.e., 0.51 $\mu$g./ml.) sulfur dioxide/TCM stock, 2.0 ml. of the formaldehyde solution, 5.0 ml. of the 5-ASSA solution and 8.0 ml. of water. A typical 25 ml. reagent blank was similarly constituted of 10.0 ml. of 0.04 M TCM solution, 2.0 ml. formaldehyde solution, 5.0 ml. of the 5-ASSA solution and 8.0 ml. of water.

Fluorometric determinations were made after 3 minutes time had elapsed from the admixture of the sulfur dioxide stock solution, formaldehyde solution and 5-ASSA solution. Fluorometer scale readings were taken immediately after zeroing with a reagent blank.

Colorimetric determinations were made after 30 minutes had elapsed from admixture of the sulfur dioxide stock solution with the para-rosaniline reagent.

D. Results

Figure 2:
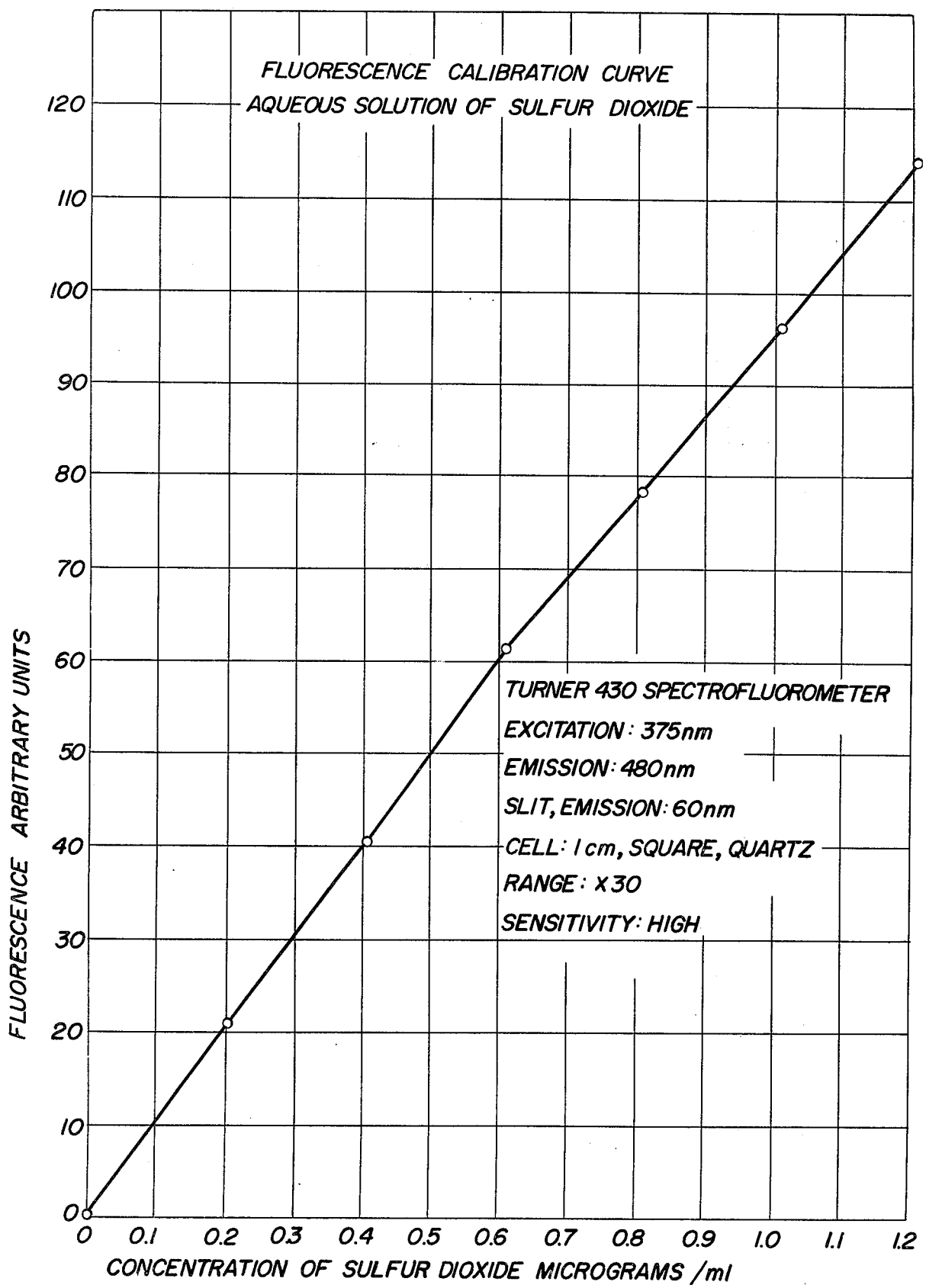
FIG. 2 is a graphic illustration of a fluorescence calibration curve for a sulfur dioxide analysis carried out according to the invention.

Results of the two analytical methods are set out in Table 1, below. The first set of concentrations employed in the fluorometric method are reproduced in the calibration curve of FIG. 2.

Table 1

| COLORIMETRIC METHOD | |
|---|---|
| Sample Content $\mu$g/ml of $SO_2$ | Colorimeter Reading Absorbance at 549 nm |
| 1.212 | 1.196 |
| 1.010 | 1.030 |
| 0.808 | 0.828 |
| 0.606 | 0.680 |
| 0.404 | 0.490 |
| 0.202 | 0.342 |
| 0.00 | 0.160 |

| FLUOROMETRIC METHOD | | |
|---|---|---|
| Sample Content $\mu$g/ml of $SO_2$ | F Range | Fluorometer Reading (excitation 375 nm, slit 15 nm; emission 480 nm; slit 60 nm; sensitivity "high") |
| | X30 | |
| 1.212 | | 114.1 |
| 1.010 | | 96.4 |
| 0.808 | | 78.1 |
| 0.606 | | 61.6 |
| 0.404 | | 40.1 |
| 0.202 | | 20.6 |
| | X300 | |
| 0.101 | | 100.0 |
| 0.0808 | | 80.0 |
| 0.0606 | | 58.5 |
| 0.0404 | | 40.5 |
| 0.0202 | | 21.0 |
| | X1000 | |
| 0.01616 | | 54.0 |
| 0.00808 | | 26.0 |

The results obtained in Example I clearly indicate the linear proportionality of the reaction between sulfur dioxide and 5-ASSA in the aqueous reaction medium. The results also indicate the exceptional sensitivity of the fluorometric method. The near-linear readings obtained for the 0.01616 and 0.00808 $\mu$g./ml. sulfur dioxide concentrations are indicative of the method's capacity for significantly distinguishing sample sulfur dioxide content variations on the order of a few parts per billion.

Figure 3:
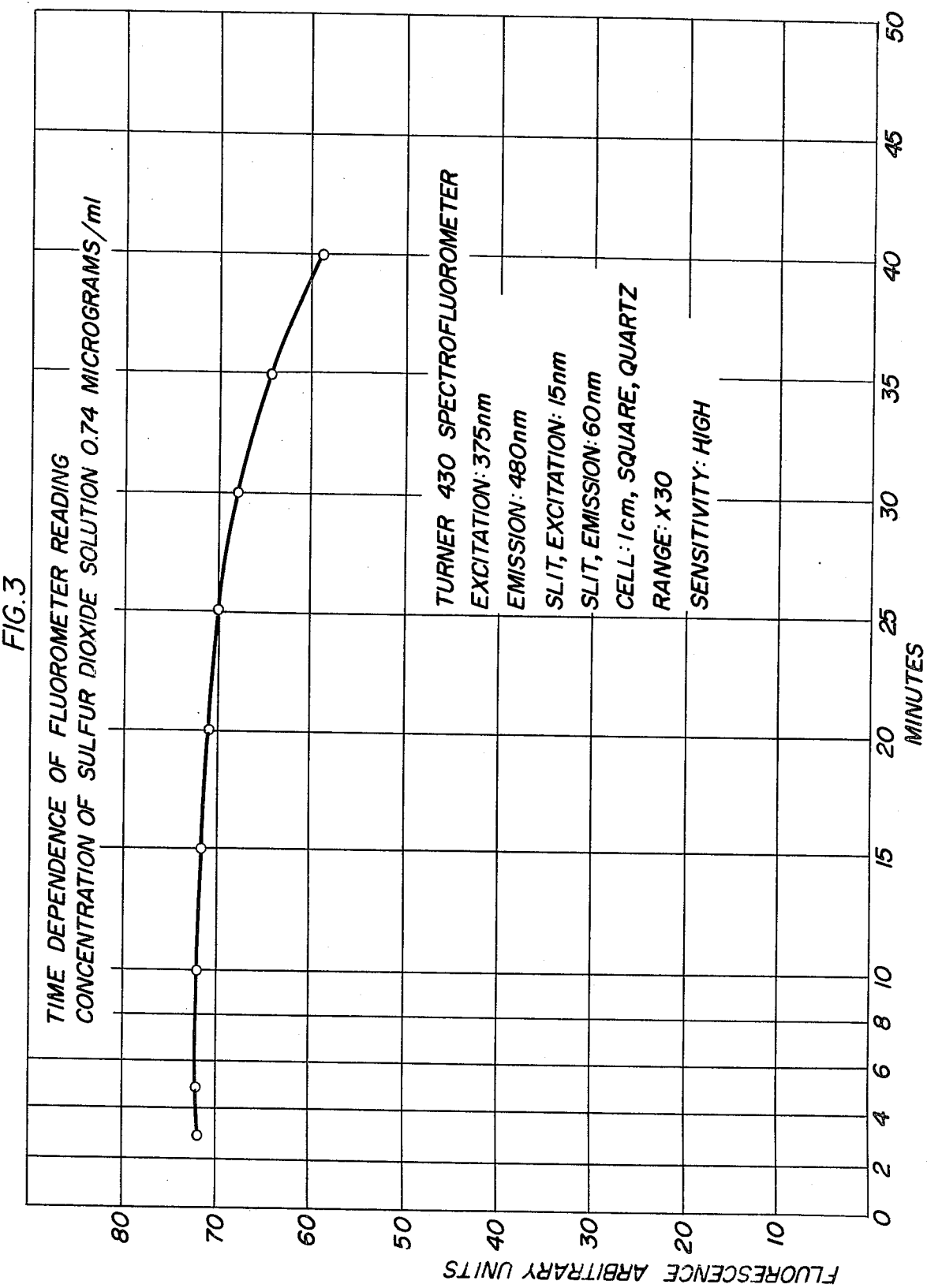
FIG. 3 is a graphic illustration of time effect upon a sulfur dioxide analysis carried out according to the invention; and, FIG. 4 is a graphic illustration of the pH dependence of fluorescence for a 0.0002 M aqueous solution of 5-amino-3-sulfo-salicylic acid.

A distinct advantage of the invention over prior art methods resides in the virtual absence of reaction "development" time and the exceptional long-term stability of the fluorescent moiety formed. FIG. 3 illustrates that the reaction involving a 0.74 $\mu$g./ml. sulfur dioxide sample is substantially completed within 3 minutes and "fades" less than 15% over a period of 40 minutes.

The following example illustrates the practice of the inventive method and its equivalence, in terms of sensitivity, to the E.P.A. reference method.

EXAMPLE II

The tests of the Example were conducted with the aid of the Cook County (Illinois) Department of Environmental Control (D.E.C.), which utilizes the E.P.A. para-rosaniline reference method. In both the reference method and the fluorometric method, the fluid sampled was air which had been passed through a 0.1 M potassium tetrachloromercurate absorbing reagent so that both sampling procedures and collection efficiency of the absorbing reagent were identical for both methods. At several Chicago area official sampling stations the D.E.C. took 24 hour averaging time samples for sulfur dioxide. The samples were analyzed for sulfur dioxide at the D.E.C. laboratory using a Technicon Autoanalyzer II and the colorimetric method as prescribed by the E.P.A. The colorimeter was calibrated with aqueous sodium meta-bisulfite solutions.

A "blind" fluorometric analysis for sulfur dioxide of the same 24 hour averaging time samples was done at the University of Illinois at the Chicago Medical Center. The D.E.C. standard meta-bisulfite solutions were used to calibrate the Turner 430 spectrofluorometer employed for the analysis. The D.E.C. tetrachloromercurate solution before sulfur dioxide absorption was used in the instrument blank. Overall, the fluorometric method used the same reagents as the reference method, with the exception of para-rosaniline, which was replaced by a 5-amino-3-sulfo-salicylic acid solution preprepared as in Example I. The excitation wave length was 375 nm and fluorescence was measured at 480 nm.

The determination of the fluorometric calibration curve is summarized in Table 2. Regression analysis was used to calculate the equation of the calibration line. Plotting the observed fluorescence data versus sulfur dioxide concentration, a graphical calibration curve was obtained. The calibration curve was a straight line passing through the origin.

Table 2

Standard Curve for $SO_2$ with Y = fluorescence, X = concentration; Y = b + mx[c]

| Concentration mg/ml | Data fluorescence[a] | STD Curve fluorescence | Data Fluorescence STD Curve |
|---|---|---|---|
| 0.00 | 0.0[b] | −0.03 | 0.03 |
| 0.30 | 38.0 | 38.07 | −0.07 |
| 0.50 | 63.5 | 63.46 | 0.04 |

[a] arbitrary units
[b] 0.0 fluorescence adjusted for blank
[c] b = −0.026316, m = 126.973684

The coefficient of correlation of the regression line, r, was 0.999998. The regression equation of the standard curve was:

$$Y = -0.026316 + 126.973684X$$

The standard deviation of fluorescence data, as calculated from the above equation, was:

$S_{y.x} = 0.08$ fluorescence units.

The concentration of sulfur dioxide, in a particular sample, was found by solving the equation of the standard curve, for the value of the independent variable, i.e. sulfur dioxide concentration, using observed fluorescence as the dependent variable. The concentration of sulfur dioxide was also read from the graph. The computed sulfur dioxide concentration of the samples is set out in Table 3.

Table 3

| Sample Name | Computed Sulfur Dioxide Concentrations | | | |
|---|---|---|---|---|
| | Data Fluorescence [a] | Fluorescence Equation [b] | Fluorescence Graph [c] | EPA Method [d], [e] |
| 26-12-5 | 87.0 | 0.685 | 0.690 | 0.685 |
| 26-13-5 | 54.2 | 0.427 | 0.430 | 0.430 |
| 26-19-5 | 20.7 | 0.163 | 0.165 | 0.165 |
| 26-10-5 | 8.8 | 0.069 | 0.070 | 0.060 |
| 26-15-5 | 5.2 | 0.041 | 0.041 | 0.045 |
| 26-17-5 | 5.2 | 0.041 | 0.041 | 0.045 |
| 26-3-5 | 4.2 | 0.033 | 0.033 | 0.034 |

[a] Arbitrary fluorescence units
[b] Y = −0.026316 + 126.973684X
[c] Read from calibration graph
[d] Read from calibration graph
[e] Results obtained by Cook County Dept. Environmental Control Test of Significance. The $t$-test was applied to the individual differences between the two sets of observations, i.e., reference method and fluorescence equation. Both methods have the same standard deviation, $s_y = 0.252$.

The value of $t$ was calculated from $$t = \frac{d}{s_d}\sqrt{n}$$

where $d$ = mean difference, $s_d$ = standard deviation of a single difference.

As calculated $t = 0.4166$. From a t-Table, corresponding to $n-1 = 6°$ of freedom, $t = 2.447$ at the 95 percent level, which supports the conclusion that there is no "systematic" difference between these two methods.

Due to the similarity of the reactions involved in the two methods, it is not unexpected that certain common constituents of fluid materials sampled for sulfur oxide content may interfere with the fluorometric method in the same way as they may interfere with the reference method. Such interferences may be "cured" according to known techniques. Interference by nitrogen dioxide, for example, may be substantially eliminated through addition to the 5-ASSA stock reagent of small quantities of sulfamic acid. In a similar manner, EDTA may be employed to prevent interference by heavy metals.

While Example II illustrates practice of the inventive fluorometric method in sulfur dioxide determinations made on air samples which have had sulfur oxides absorbed in a tetrachloromercurate reagent, it will be apparent to those skilled in the art that the method employed is equally applicable to liquid samples (such as wastewater) and to fluid samples generally which have not been "pre-treated" to remove or absorb sulfur oxides prior to the determination.

Figure 1:
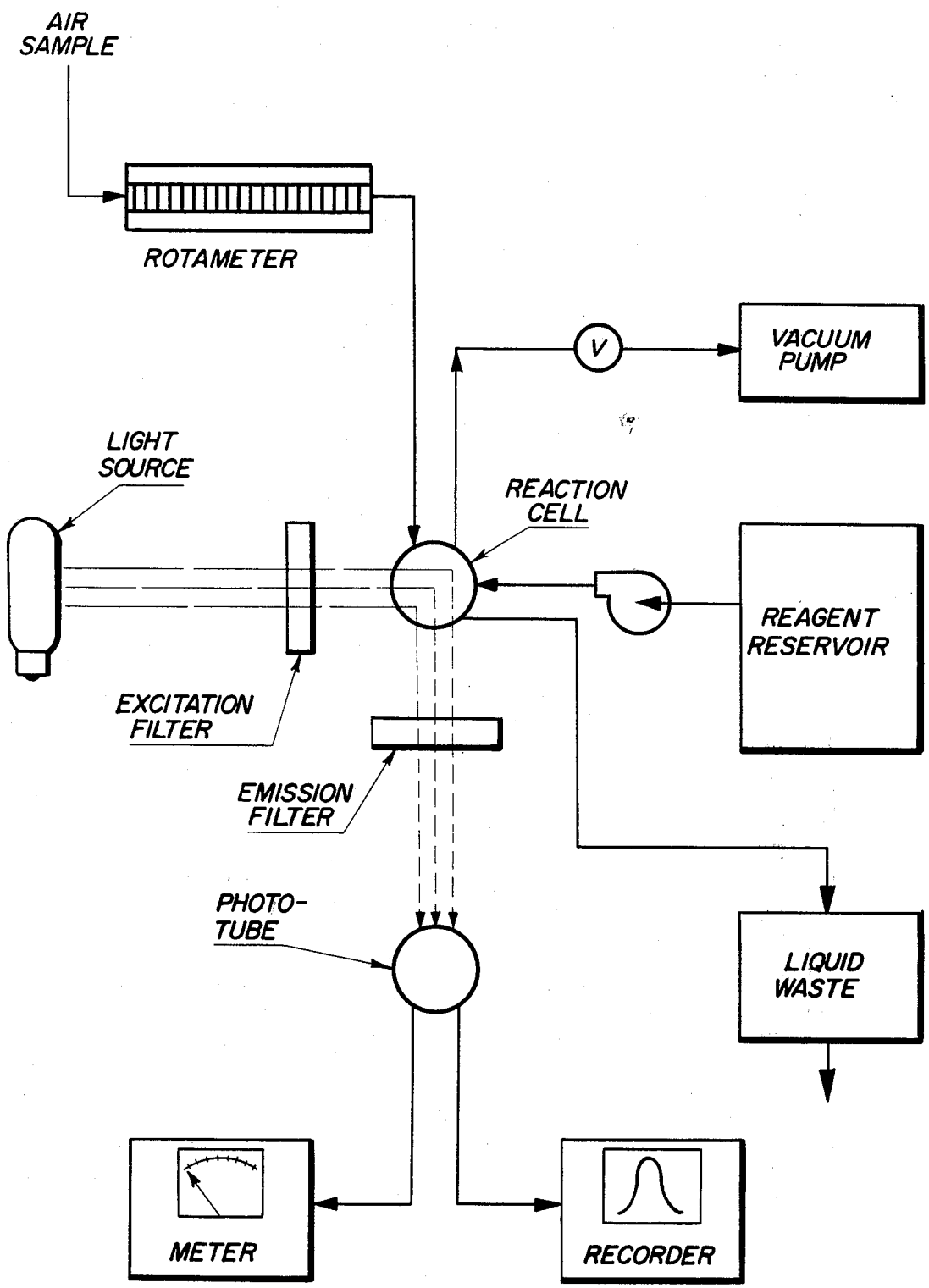
FIG. 1 is a schematic representation of an instrumental system for sulfur oxide determination according to the present invention.

FIG. 1 schematically illustrates a detection system constructed according to the present invention for relatively continuous sulfur dioxide determinations on air samples. Included in the system is a fluorometric reactor cell, preferably constructed of quartz. The cell is fitted with appropriate ports to allow entry of the desired reagent or reagents from a reservoir and fixed quantities of an air sample from a rotameter collector. A light source generates excitation energy which passes through an excitation monochrometer or filter before striking the cell. Light energy leaving the cell passes through an emission monochrometer or filter to a phototube. Fluorescence is indicated either on a meter or, alternatively, on a recorder. Suitable means (not shown) may be provided to exhaust and rinse the cell prior to the next test procedure. If desired, a scrubber may be provided for relatively long term absorption of sulfur dioxide with a trapping agent such as TCM.

In use, the cell is charged with reagents alone as a reagent blank for zeroing the fluorometer. Thereafter a fixed quantity of an air sample is bubbled through the cell and the reaction product is fluorometrically analyzed.

Reagents for use in the invention include aqueous solutions of selected free amino-containing compounds, such as 5-ASSA, having a pH regulated to substantially inhibit fluorescence of the compound in unreacted form but not substantially inhibit the fluorescence of the moiety formed by the Schiff reaction of the compound with sulfur oxide and appropriate aldehyde. Presently preferred reagents are formulated with 5-ASSA dissolved in 1.7% phosphoric acid. The molarity of 5-ASSA in the reagent may vary substantially, the only limiting factor being generally the provision of a stoichiometric excess of the compound vis-a-vis the expected sulfur oxide content of the sample. While phosphoric acid is a preferred reagent component, other acids such as sulfuric and hydrochloric may be employed. As earlier noted, the pH of the reagent should be adjusted to a value low enough to dampen the fluorescence of the free amino-containing compound, but not the fluorescence of the desired reaction product. Determination of suitable pH, excitation wavelength, emission wavelength, and the like parameters for any given selected compound must be made in a routine manner.

A reagent comprising phosphoric acid and 5-ASSA having a pH of from 1 to 3 and preferably about 1.7 has been found to be quite useful and shelf-stable. A similar reagent additionally containing formaldehyde has also proved operative and stable, although some reagent mixtures of this type have exhibited a slightly pink color upon 3 or 4 days standing.

While formaldehyde is the preferred aldehyde reagent for use in the invention, it is expected that others such as acetaldehyde may be suitably employed without significantly diminishing the utility of the methods, reagents or systems.

Selection of a suitable free amino-containing compound should proceed according to the criteria earlier mentioned, i.e., solubility, lack of substantial inherent fluorescence under appropriate reaction conditions, limited number of free amino groups, etc. Inasmuch as 5-ASSA has proven to be quite useful, it is expected that analogues and homologues of this monoamine-substituted benzene sulfonic acid compound may be similarly useful. Use of such selected compounds may involve fluorometric analysis employing excitation and emission wavelengths other than the preferred respective 375 nm and 480 nm wavelengths employed when using 5-ASSA.

Obviously, numerous modifications and variations of the systems, methods and reagents of the present invention will occur to those skilled in the art without departing from the spirit and scope of the disclosure. Thus, as one example, it is clearly within the contemplation of the disclosure to employ the fluorometric techniques and reagents above-described in systems designed to detect and quantify an aldehyde, such as formaldehyde, in a fluid sample. Such a system would involve contacting the aldehyde-containing fluid sample with a reagent containing a stoichiometric excess of both 5-ASSA and a suitable sulfur oxide, such as sulfurous acid. As a further example, it is within the contemplation of the disclosure to employ spectrophotometric techniques for quantification of sulfur oxides through comparative spectral quantification of the reaction product of a sulfur oxide, a suitable aldehyde, and a suitable compound such as 5-ASSA, vis-a-vis a reagent blank containing only the unreacted aldehyde and 5-ASSA. Therefore only such limitations as appear in the appended claims should be placed on the invention.

What is claimed is:

1. A reagent suitable for use in quantitatively determining the sulfur oxide content of a fluid sample, said reagent essentially consisting of:
    an aqueous solution of an acid and 5-amino-3-sulfo-salicylic acid, said solution having a pH of from about 1 to about 3.

2. A reagent according to claim 1 further including an aldehyde.

3. A reagent according to claim 2 wherein said aldehyde is formaldehyde.

4. A reagent according to claim 1 wherein the pH of said solution is about 1.7.

5. A reagent according to claim 1 wherein said acid comprises phosphoric acid.

6. A method for quantitatively determining the sulfur oxide content of a fluid sample, said method comprising:
    forming an aqueous reaction mixture essentially consisting of said fluid sample, an acid, an aldehyde and 5-amino-3-sulfo-salicylic acid, said reaction mixture having a pH of about 1 to about 3; and
    quantitatively analyzing said reaction mixture for the presence of fluorescent materials therein.

7. The method of claim 6 wherein said aldehyde is formaldehyde.

8. The method of claim 6 wherein said reaction mixture has a pH of about 1.7.

9. The method of claim 6 wherein said acid comprises phosphoric acid.

10. The method of claim 6 wherein said quantitative analysis step includes subjecting said reaction mixture to excitation by light having a wavelength of about 375 nm and thereafter monitoring said reaction mixture for emission of light having a wavelength of about 480 nm.

11. The method of claim 6 further including comparing the results of said quantitative analysis step to the results of the quantitative analysis for fluorescent materials in a separately prepared aqueous reaction mixture essentially consisting of an acid, an aldehyde, 5-amino-3-sulfo-salicylic acid and a fluid sample containing a known quantity of sulfur oxide, said separate reaction mixture having a pH of from about 1 to about 3.

12. Apparatus for the direct fluorometric determination of the sulfur oxide content of a fluid sample, said apparatus comprising:
    fluid container means transparent to light of a wavelength of from about 375 to about 480 nm;
    separate means for introducing a fluid reagent and a fluid sample containing sulfur dioxide into said container, wherein they react;
    means for monitoring the emission of light, having a wavelength of about 480 nm, from a fluid within said container means.

* * * * *

UNITED STATES PATENT OFFICE
CERTIFICATE OF CORRECTION

Patent No. 3,973,911     Dated August 10, 1976

Inventor(s) Alfred Von Smolinski et al.

It is certified that error appears in the above-identified patent and that said Letters Patent are hereby corrected as shown below:

Column 1, line 2, before "BACKGROUND" insert the following:

-- The invention described herein was made in the course of work under a grant from the Department of Health, Education, and Welfare. --.

Column 5, line 23, "114,1" should read -- 114.1 --;

Claim 12, following line 8, insert -- means for exciting the fluid within said container means with light having a wavelength of about 375 nm; --.

Signed and Sealed this

Second Day of November 1976

[SEAL]

Attest:

RUTH C. MASON
Attesting Officer

C. MARSHALL DANN
Commissioner of Patents and Trademarks